US006933285B2

(12) United States Patent
Platz

(10) Patent No.: US 6,933,285 B2
(45) Date of Patent: Aug. 23, 2005

(54) FLAVIN N-OXIDES: NEW ANTI-CANCER AGENTS AND PATHOGEN ERADICATION AGENTS

(75) Inventor: Matthew S. Platz, Columbus, OH (US)

(73) Assignee: The Ohio State University, Columbus, OH (US)

(*) Notice: Subject to any disclaimer, the term of this patent is extended or adjusted under 35 U.S.C. 154(b) by 0 days.

(21) Appl. No.: 10/436,401

(22) Filed: May 12, 2003

(65) Prior Publication Data

US 2004/0006028 A1 Jan. 8, 2004

Related U.S. Application Data

(60) Provisional application No. 60/379,321, filed on May 10, 2002.

(51) Int. Cl.$^7$ ..................... A61K 31/706; A61K 31/70; A61K 31/525
(52) U.S. Cl. .......................... 514/43; 514/42; 514/250; 514/251
(58) Field of Search ........................... 514/43, 42, 250, 514/251

(56) References Cited

U.S. PATENT DOCUMENTS

| | | | |
|---|---|---|---|
| 5,945,420 | A | 8/1999 | Araki et al. |
| 6,177,441 | B1 | 1/2001 | Cook et al. |
| 6,258,577 | B1 | 7/2001 | Goodrich, et al. |
| 6,503,699 | B1 | 1/2003 | Wollowitz et al. |
| 6,514,987 | B1 | 2/2003 | Cook et al. |
| 2002/0028432 | A1 | 3/2002 | Cook et al. |
| 2002/0182581 | A1 | 12/2002 | Cook et al. |

OTHER PUBLICATIONS

Gura (Science, 1997, 278(5340):1041–1042).*
Jain (Sci. Am., 1994, 271:58–65).*
Curti (Crit. Rev. in Oncology/Hematology, 1993, 14:29–39).*
Hartwell et al (Science, 1997, 278(5340):1064–1068).*
Fersi, Hannan, M.S., "Binding Affinities of Sensitizers of Pathogen Eradication and Photochemical Behavior of Riboflavin and Riboflavin–N–Oxide," A Thesis, 2002, The Ohio State University.
Brown, J.M., "SR 4233 (Tirapazamine): a new anticancer drug exploiting hypoxia in solid tumours," Br. J. Cancer 67, pp. 1163–1170, 1993, Macmillan Press Ltd.
Daniels, J. Scott et al., "DNA Cleavage by the Antitumor Agent 3–Amino–1,2,4–benzotriazine 1,4–Dioxide (SR4233): Evidence for Involvement of Hydroxyl Radical," J. Am. Chem. Soc., 118, pp. 3380–3385, 1996, American Chemical Society.
Brown, J.M., "Exploiting the hypoxic cancer cell: mechanisms and therapeutic strategies," Molecular Medicine Today, vol. 6, pp. 157–162, London, UK, 2000.
Kelson, Andrew B. et al., "1,2,4–Benzotriazine 1,4–dioxides. An important class of hypoxic cytotoxins with antitumor activity," Anti–Cancer Drug Design, 13, pp. 575–592, Oxford Univ. Press, 1998.
Brown, J.M., "The Hypoxic Cell: A Target for Selective Cancer Therapy—Eighteenth Bruce F. Cain Memorial Award Lecture," Cancer Research, 59, pp. 5863–5870, Stanford, CA, Dec. 1, 1999.
Brown, J.M. et al., "Tirapazamine: laboratory data relevant to clinical activity," Anti–Cancer Drug Design, 13, pp. 529–539, Oxford Univ. Press, 1998.
Evans, James W. et al., "Tirapazamine is Metabolized to Its DNA–damaging Radical byIntranuclear Enzymes," Cancer Research, 58, pp. 2098–2101, Stanford, CA, May 15, 1998.
Daniels, J.S. et al., "Photochemical DNA Cleavage by the Antitumor Agent 3–Amino–1,2,4–Benzotriazine 1,4–Dioxide (Tirapazamine, WIN 59075, SR4233)," The Journal of Organic Chemistry, vol. 63, No. 26, pp. 10027–10030, American Chemical Society, 1998.
Patterson, Laurence H. et al., "Electron Paramagnetic Resonance Spectrometry Evidence for Bioreduction of Tirapazamine to Oxidising Free Radicals Under Anaerobic Conditions," Biochemical Pharmacology, Vo. 60, pp. 1933–1935, Elsevier Science Inc., 2000.
Fieschi, Franck et al., "The Mechanism and Substrate Specificity of the NADPH: Flavin Oxidorductase from Escherichia Coli"., Journal of Biological Chemistry, Dec. 1995, vol. 270, No. 51, pp. 30392–30400.

(Continued)

Primary Examiner—James O. Wilson
Assistant Examiner—Michael C. Henry
(74) Attorney, Agent, or Firm—Calfee, Halter & Griswold LLP

(57) ABSTRACT

Compounds comprising flavin N-oxides for treatments of solid tumors, non-solid tumor masses, leukemias, and non-small cell lung cancers and for eradicating contaminants in blood products. Methods of treating patients having solid type cancers comprising administering a therapeutically effective amount of a flavin N-oxide to a subject in need of treatment and exposing the flavin N-oxide to an activator such that activation of the flavin N-oxide results in damage to the DNA in the cancer cells without substantial damage to the DNA of normal cells are also provided. Methods of using a flavin N-oxide as part of a combination therapy with chemotherapy, radiation therapy, or both are also provided. Methods of reducing pathogenic bacterial or viral contamination in a composition comprising a) mixing the composition with an efficacious amount of a flavin N-oxide and b) exposing the mixture of the composition and the flavin N-oxide to an activator for a period of time sufficient to activate the flavin N-oxide such that the flavin N-oxide reduces the contamination in the composition are also provided. Preferably, the composition is a blood product selected from plasma, platelets, and red blood cells and the activator is an enzyme.

13 Claims, 3 Drawing Sheets

OTHER PUBLICATIONS

Xun, Luying et al., "Characterization of 4–Hydroxyphenylacetate 3–Hydroxylase (HpaB) of *Escherichia coli* as a Reduced Flavin Adenine Dinucleotide–Utilizing Monooxygenase," *Applied and Environmental Microbiology*, Feb. 2000, vol. 66, No. 2, pp. 481–486.

Niviere, Vincent et al.., "Is the NAD(P)H: Flavin Oxidoreductase from *Escherichia coli* a Member of the Ferredoxin–NADP+ Reductase Family?" *The Journal of Biological Chemistry*, Jul. 12, 1996, vol. 271, No. 28, pp. 16656–16662, The American Society for Biochemistry and Molecular Biology, Inc.

Niviere, Vincent et al.., "The NAD(P)H: Flavin Oxidoreductase from *Escherichia coli*," *The Journal of Biological Chemistry*, Jun. 25, 1999, vol. 274, No. 26, pp. 18252–18260, *The American Society for Biochemistry and Molecular Biology, Inc.*

Woodmansee, Anh N. et al., "Reduced Flavins Promote Oxidative DNA Damage in Non–respiring *Escherichia coli* by Delivering Electrons to Intracellular Free Iron," *The Journal of Biological Chemistry*, Sep. 13, 2002, vol. 277, No. 37, pp. 34055–34066, The American Society for Biochemistry and Molecular Biology, Inc.

Kasim, Mumtaz, "The Role of the N(5) Interaction and Associated Conformational Changes in the Modulation of the Redox Properties in Flavoproteins," Dissertation, 2002, 208 pages.

\* cited by examiner

The sensitizer breaks down to form riboflavin

+HO•
DNA Damage
Pathogen Eradication
Hypoxic Tumor Treatment

FLAVIN N-OXIDES: NEW ANTI-CANCER AGENTS AND PATHOGEN ERADICATION AGENTS

CROSS-REFERENCE TO RELATED APPLICATIONS

This application claims priority to U.S. Provisional Application Ser. No. 60/379,321 filed May 10, 2002, the entirety of which is incorporated herein by reference.

BACKGROUND

Solid tumors account for more than 90% of all human cancers. As the tumor grows, in order to sustain itself, it must develop its own blood supply. This blood supply, however, is much different from the blood supply to normal tissues. The blood vessels formed in tumors are typically highly irregular and tortuous. They may have arterio-venous shunts and blind ends, and lack smooth muscle or nerves and have incomplete endothelial linings and basement membranes. This leads to low overall levels of oxygen in most tumors. Many tumors have areas of extreme hypoxia. (Brown, J. M. "Exploiting the hypoxic cancer cell: mechanisms and therapeutic strategies." *Molecular Medicine Today* Apr. 2000 (Vol. 6)).

Unfortunately, there is considerable evidence that hypoxic tumors are refractory towards many of the currently available treatments for solid tumor cancers, including radiation therapy and chemotherapy. Accordingly, there exists a need for a method of treating solid tumor cancers having hypoxic regions.

A second problem existing in medicine today is the need for reliable methods for eradication of pathogens in blood products. In the United States almost 4 million individuals are transfused every year with over 28 million blood components derived from nearly 13 million units of blood donated by apparently healthy volunteers. The blood components are extensively tested for the presence of pathogens prior to administration. Testing has reduced the risk of transmission of enveloped virus to a small but finite value in the developed world. The NIH has estimated the risk during transfusion of a unit of screened blood is 1/1,000,000 for hepatitis A virus (HAV), 1/30,000–1/50,000 for HBV, and 1/2,000,000 for human T-cell lymphotropic viruses (HTLV). The odds of transmission for parvovirus B19 is much larger 1/10,000. Parvovirus and HCV lack a lipid membrane envelope and have relatively poor odds of transmission, relative to other pathogens.

The solvent detergent (SD) method is used to eradicate enveloped virus and bacterial pathogens present in units of plasma protein. The lipid envelope of the pathogen is dissolved by the solvent detergent. The SD method cannot be used to eradicate pathogens present in platelet and red cell concentrates because the cells also contain lipid envelopes and will be lysed by the pathogen inactivation treatment. The SD method does not inactivate HCV and parvovirus in units of plasma protein because they do not contain a lipid envelope. Thus, there is an urgent need to develop technology that may eradicate non-enveloped pathogens in units of blood components.

SUMMARY

Provided herein are methods of treating solid tumors, non-solid tumor masses, leukemias, and non-small cell lung cancers in subjects in need of such treatment by administering an therapeutically effective amount of a flavin N-oxide, as shown in formula I:

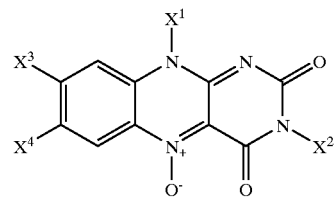

wherein $X^1$ is selected from H, monosaccharides, substitited monosaccharides, mono, di, and tri-ethylene glycol, alcohol, and alkyl ammonium ion; and $X^2$, $X^3$, and $X^4$ can be the same or different and are selected from H, monosaccharides, substituted monosaccharides, glycol, alcohol, lower alkyl, and alkylene groups further substituted with monosaccharides, substituted monosaccharides, mono, di, and tri-ethylene glycol, alcohol, or alkyl ammonium ion.

It is preferred that the substituents are chosen such that the flavin N-oxide is water soluble. An example of a flavin N-oxide of formula I is riboflavin N-oxide, which is shown in formula II:

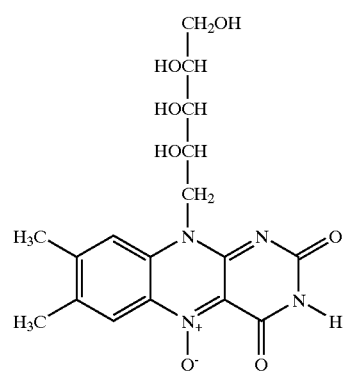

The method of treating a subject having solid tumors, non-solid tumor masses, leukemias, and non-small cell lung cancers comprises administering a therapeutically effective amount of a flavin N-oxide to a subject in need of such treatment. Once administered, the flavin N-oxide is exposed to an activator, which results in damage to the DNA of cancer cells without substantial damage to the DNA of normal cells in the subject. Riboflavin N-oxide is an example of a flavin N-oxide.

The activator may be a reducing enzyme or electromagnetic radiation. The activator is preferably a reducing enzyme. The reducing enzymes are preferably reducing enzymes that are in the cancer cells, though the reducing enzyme may be a reducing agent outside of the cell. When electromagnetic radiation is used as the activator in this method, it is preferably X-ray radiation. A combination of both electromagnetic radiation and reducing enzymes can serve as the activator.

Preferably, the method will preferentially kill cancer cells rather than normal cells in a ratio of at least 5:1. More preferably, it will kill cancer cells rather than normal cells in a ratio of at least 10:1.

The method of treating solid tumors, non-solid tumors masses, leukemias, and non-small cell lung cancers in subjects may be used as part of a combination therapy, which further includes chemotherapy, radiation therapy, or both.

Methods of using flavin N-oxides to reduce pathogenic bacterial and viral contamination in blood products are also provided. The method of reducing pathogenic bacterial or viral contamination in blood products comprises the steps of introducing an efficacious amount of a flavin N-oxide to a composition of blood products containing pathogenic bacterial or viral contamination and then exposing the resulting mixture to an activator for a period of time sufficient to activate the flavin N-oxide and thus reduce the contamination in the composition. The blood product does not require further purification after pathogen eradication with flavin N-oxides. Alternatively, the method may further comprise a purification step after eradication of the blood products with the flavin N-oxide.

The flavin N-oxide can be activated by reducing enzymes present in the bacteria and viruses, by activating with electromagnetic radiation, or through a combination of reducing enzymes and electromagnetic radiation. Preferably, when electromagnetic radiation is used, it is visible light. The reducing enzymes may be those present in the bacterial or viral contaminants or may be reducing agents added for the purpose of activation.

The method eradicating pathogenic bacterial or viral contamination in blood products is especially useful for the eradication of such pathogens as HAV, HBV, HTLV, parvovirus B19, and HCV.

DETAILED DESCRIPTION

The present invention relates to the class of compounds flavin N-oxides and methods of administering flavin N-oxide compounds to cells in a variety of different environments. Flavin N-oxides, such as riboflavin N-oxide, are preferentially absorbed by bacteria and rapidly proliferating cells, which the compounds passively enter. Inside the cells, the flavin N-oxides are activated by enzymes present within the cells. Once activated, the flavin N-oxides promote damage of the nucleic acids of the cell, making them useful in a variety of applications.

Flavin N-oxides comprise the compound of general formula I:

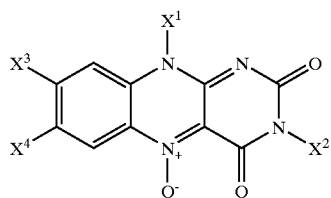

wherein $X^1$ is selected from H, monosaccharides, substitited monosaccharides, mono, di, and tri-ethylene glycol, alcohol, and alkyl ammonium ion; and $X^2$, $X^3$, and $X^4$ can be the same or different and are selected from H, monosaccharides, substituted monosaccharides, glycol, alcohol, lower alkyl, and alkylene groups further substituted with monosaccharides, substitited monosaccharides, mono, di, and tri-ethylene glycol, alcohol, or alkyl ammonium ion.

An example of a flavin N-oxide is riboflavin N-oxide (RBO), which is shown in formula II:

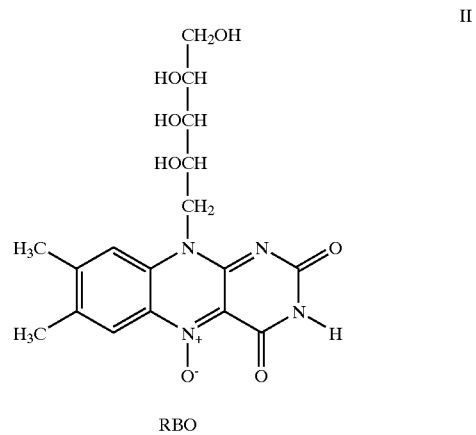

RBO

The flavin N-oxides used in accordance with the present invention are preferably water soluble. It is desirable to have water soluble cancer drugs in order to decrease the overall amount of fluid that must be administered, as well as to decrease the administration time. Preferably, the solubility of these compounds is 100 micromolar or greater.

In accordance with some embodiments described herein, it may be preferred, but not essential, that the compounds used are electrically neutral to ease transport into cells. In some embodiments, electrically charged species, such as ammonium salts may be used.

Riboflavin N-oxide, is one example of a flavin N-oxide, it is water soluble and electrically neutral. Additionally, upon fragmentation of the neutral radical, riboflavin N-oxide forms the hydroxyl radical, which damages the nucleic acid, and riboflavin, vitamin B2, which is generally regarded as safe in humans.

Figure 1:
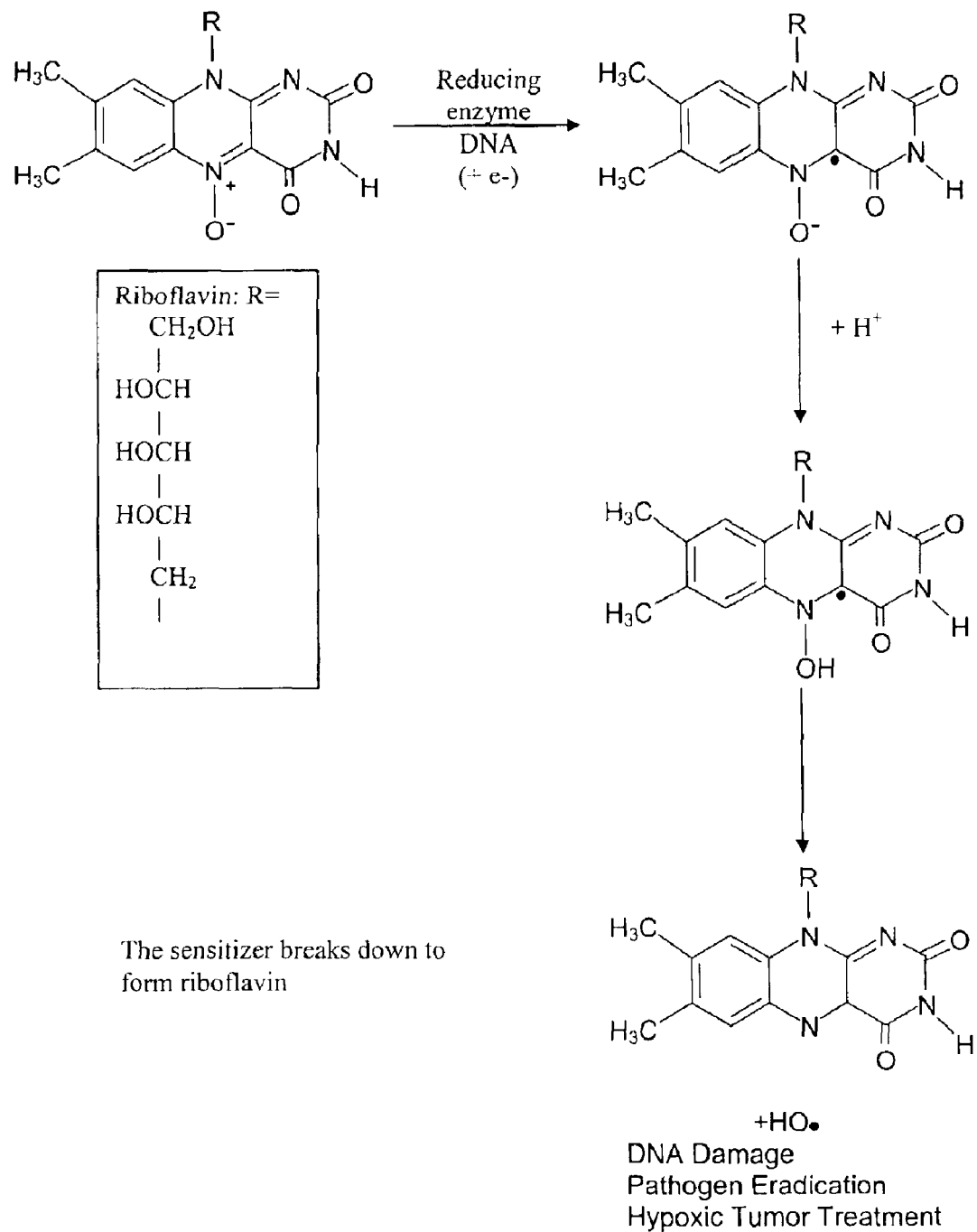
FIG. 1 shows a proposed mechanism of flavin N-oxide activation and decomposition into a molecule of the flavin and a hydroxyl radical.

Flavin N-oxides are well suited for methods of treating solid tumors, especially hypoxic tumors, and purifying blood products because these methods each ultimately depend on the same mechanism. That mechanism, outlined in FIG. 1, begins with activation of the flavin N-oxide followed by the release of the hydroxyl radical, which ultimately damages the nucleic acids in the cells.

As shown in the mechanism, the flavin N-oxides react with electromagnetic radiation or reducing enzymes within cells to form a radical anion. This radical anion, then, when in contact with an acidic complex, will be protonated. This converts the radical to a neutral radical, which fragments. The fragmentation results in the formation of a flavin and hydroxyl radical. The hydroxyl radical damages the nucleic acid. When the flavin is riboflavin N-oxide, the flavin formed is riboflavin, vitamin B2, which is generally regarded as safe. Since the acidic complexes in the cells are generally DNA complexes, such as spermidine-DNA complexes, the hydroxyl radical is formed very close to the DNA, which is very effective in damaging one or both strands of the DNA. Comparatively, if the activation occurred far from the DNA, the hydroxyl radical may react with something else before it reaches the DNA. Furthermore, it is believed that these complexes tend to cluster together on a strand of DNA, which results in more severe damage, including more breaks overall and more double-strand breaks, which the cell is unlikely to be able to repair.

When the flavin N-oxide is activated by electromagnetic radiation, the range of electromagnetic radiation chosen will depend on what the medium in which the flavin N-oxide is used in. For example, when treating patients with solid tumor cancers, X-rays, already used in radiation therapy, may be used as the activator. When the flavin N-oxide is used in the eradication of pathogens in blood products, the electromagnetic radiation used to activate the flavin N-oxide may be a visible wavelength.

I. Treatment of Solid Tumor Cancers

The first method of the present invention is a treatment of solid tumor cancers, non-solid tumor masses, leukemias, and non-small cell lung cancers. The flavin N-oxides, unlike most of the currently available chemotherapeutic agents, are effective in treating hypoxic cells in solid tumors. The flavin N-oxides are able to passively transport into the hypoxic cells and damage the nucleic acids of those cells through the mechanism in FIG. 1.

The mechanism by which the activated radical releases a hydroxyl radical, which ultimately damages nucleic acids, however, is inhibited by oxygen. The implication of this is that the flavin N-oxides will selectively harm the nucleic acids in hypoxic cells, ultimately killing those cells, without substantially harming normal cells that contain normal amounts of oxygen.

EXAMPLE 1

PA-Lymphoblastoid Cell Line: Study of the effect of oxygen deprivation in the presence of 3 sensitizers Six solutions were prepared having the solutions and the cells from each of the 6 sets were "bubbled" with nitrogen separately for 15 minutes before being mixed.

| Time (hour) | 0 | 4 | 20 | |
|---|---|---|---|---|
| Riboflavin (RB) | 1 | 0.9 | 0.63 | million cells/mL |
| RB + gluta | 0.6 | 0.5 | 0.8 | million cells/mL |
| RBO | 0.45 | 0.46 | 0.06 | million cells/mL |
| RBO + gluta | 0.65 | 0.5 | 0.2 | million cells/mL |
| Tirapazamine (TPZ) | 0.4 | 0.4 | 0.36 | million cells/mL |
| TPZ + gluta | 0.5 | 0.5 | 0.3 | million cells/mL |

The results of this study are shown graphically in FIG. 5. This indicates high hypoxic toxicity of RBO.

Because of the selectivity of the flavin N-oxides to kill hypoxic cells rather than aerobic cells, it may be preferable to use the methods of the present invention as part of a combination therapy. The methods of the present invention would be conducive to combination therapies including both chemotherapy and radiation therapy. Alternatively, the methods of the present invention would work with either radiation therapy, which would give potential for additional activation of the flavin N-oxides, or chemotherapy.

It is preferred that the flavin N-oxides chosen kill cancer cells preferentially over normal cells at a ratio of at least five to one. It is more preferred that the compound of the present invention kill cancer cells preferentially over normal cells at a ratio of at least ten to one. A larger cancer cytotoxicity ratio (defined as a ratio of the compound's preference to kill cancer cells over the compound's preference to kill normal cells) will be even more preferable.

The phrase combination therapy, in defining use of a compound of the present invention and one or more other pharmaceutical agent, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

There are large numbers of antineoplastic agents available in commercial use, in clinical evaluation and in pre-clinical development, which could be selected for treatment of cancers or other disorders characterized by rapid proliferation of cells by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Suitable agents which may be used in combination therapy will be recognized by those of skill in the art. Similarly, when combination therapy is desired, radioprotective agents known to those of skill in the art may also be used.

The term "treatment" includes partial or total destruction of the undesirable proliferating cells with minimal destructive effects on normal cells. In accordance with the present invention, a desired mechanism of treatment at the cellular level is apoptosis.

The terms "therapeutically effective" and "pharmacologically effective" are intended to qualify the amount of each agent which will achieve the goal of improvement in disease severity and the frequency of incidence over treatment of each agent by itself, while avoiding adverse side effects typically associated with alternative therapies.

The term "subject" for purposes of treatment includes any human or animal subject who has a solid tumor cancer. Besides being useful for human treatment, the compounds of the present invention are also useful for veterinary treatment of mammals, including companion animals and farm animals, such as, but not limited to dogs, cats, horses, cows, sheep, and pigs. Preferably, subject means a human.

Also included in the family of compounds of Formulae I and II are the pharmaceutically acceptable salts thereof. The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of the flavin N-oxide compounds may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, galactaric, and galacturonic acids. Suitable pharmaceutically acceptable base addition salts of the flavin N-oxide compounds include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the compounds of the flavin N-oxides. All of these salts may be prepared by conventional means from the corresponding compounds of the flavin N-oxides by reacting, for example, the appropriate acid or base with the desired flavin N-oxide.

The pharmaceutical composition comprises a therapeutically effective amount of a flavin N-oxide, or a derivative or pharmaceutically acceptable salt thereof, in association with at least one pharmaceutically acceptable carrier, adjuvant, or diluent (collectively referred to herein as "carrier materials") and, if desired, other active ingredients. Riboflavin N-oxide is an especially preferred flavin N-oxide. The flavin N-oxides may be administered by any suitable route known to those skilled in the art, preferably in the form of a pharmaceutical composition adapted to such a route, and in a dose effective for the treatment intended. The active compounds and composition may, for example, be administered orally, parenterally, or by other methods known in the art.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

The methods of the present invention also encompass the use of derivatives of the flavin N-oxides. Derivatives are intended to encompass any compounds which are structurally related to the flavin N-oxides or which possess the substantially equivalent activity, as measured by the derivative's ability to damage the nucleic acids in cancer cells, especially hypoxic cancer cells preferentially over normal cells. By way of example, such compounds may include, but are not limited to, prodrugs thereof. Such compounds may be formed in vivo, such as by metabolic mechanisms.

The dosage form and amount may be readily established by reference to known treatment regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, and the particular compound employed, the location of the solid tumor cells, as well as the pharmacokinetic properties of the individual treated, and thus may vary widely. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose may be administered in one to four doses per day.

II. Eradication of Contaminants in Blood Products

The second aspect of the present invention relates to flavin N-oxide sensitizers for inactivation of pathogenic bacteria and viruses in units of blood products, such as platelets, plasma proteins, and red blood cells.

Photosensitized Pathogen Inactivation—An Overview Pathogens are composed of the same amino acid, nucleic acid, and lipid building blocks as plasma proteins, platelets, and red cells. Consequently, there is no known wavelength of light that may be selectively deposited into pathogens in the presence of blood products. UVB (280–320 nm) and UVC (200–280 nm) radiation is absorbed by pathogens, plasma proteins and platelets. This inactivates pathogens but with unacceptable damage to plasma proteins and platelets. Red cells absorb this type of radiation so strongly one cannot inactivate pathogens with UVB and UVC radiation in their presence. UVA radiation (320–400 nm) alone does not inactivate virus. It does, however, shorten the shelf life of platelets.

Figure 2:
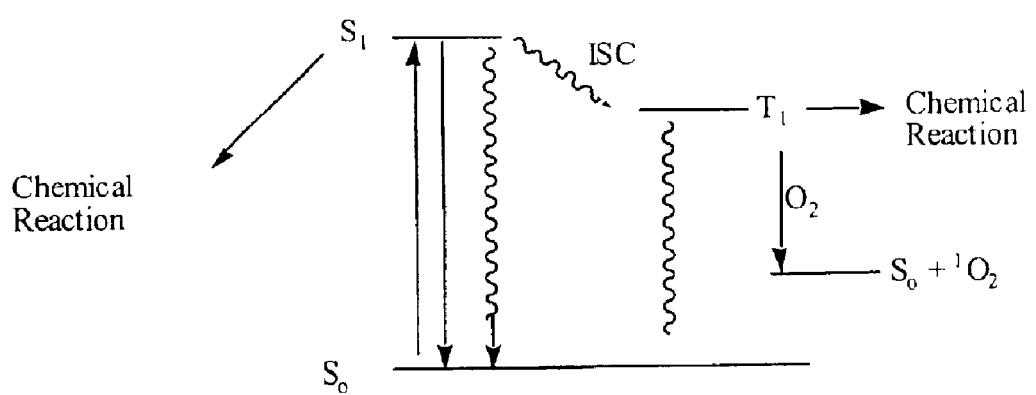
FIG. 2 depicts a Jablonski diagram.
Figure 3:
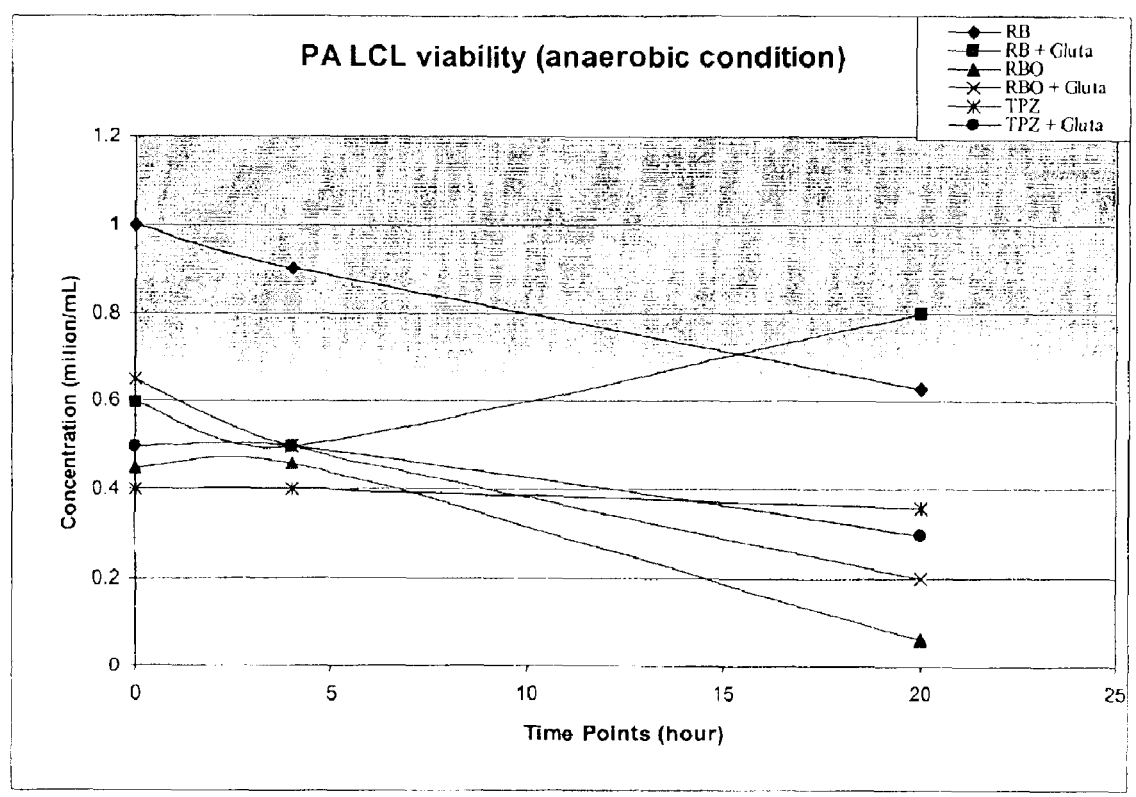
FIG. 3 shows the PA-Lymphoblastoid viability after treatment of the cells with riboflavin, riboflavin N-oxide and tirapazamine.

This fact has led practitioners to study sensitizers. By definition, sensitizers absorb light and initiate chemical reactions that inactivate pathogens. Sensitizer photophysics and photochemistry may be usefully summarized with the aid of a Jablonski diagram, as shown in FIG. 2. The sensitizer in its ground electronic state is referred to as $S_0$. Upon absorption of light it is converted to an electronically excited state, which in condensed phase, immediately ($<<10^{-11}$ s) relaxes to the lowest vibrational level of the lowest excited state ($S_1$). The lifetimes of $S_1$ states in solution are usually in the range of 1–10 ns and are controlled by internal conversion (IC) and fluorescence (F) decay back to $S_0$, to intersystem crossing (ISC) to a paramagnetic triplet state ($T_1$) and by inter and intramolecular chemical reactions. Because $S_1$ is short-lived, bimolecular reactions of $S_1$ will be inefficient unless the trapping agent is rather concentrated (0.1–1.0 M) or the sensitizer and the trap are complexed. A sensitizer bound to protein or nucleic acid will likely react in its $S_1$ state. A common reaction of this type is electron transfer. Fluorescence quenching is characteristic of bimolecular reactions of $S_1$.

Sensitizer triplet states are much longer lived than excited singlet states. Their lifetimes are typically controlled by bimolecular reactions, particularly reaction with oxygen, a molecule with a triplet ground state. This reaction leads to the formation of singlet oxygen, a potent oxidizing agent that is employed in many lipid targeted photosensitized viral inactivation strategies.

Known Photochemical Sensitizers of Viral Inactivation Currently, practitioners in the platelet field utilize UVA radiation (350–400 nm) and sensitizers to inactivate viruses. Two psoralens, AMT and S-59, which have the following structures, have been utilized extensively.

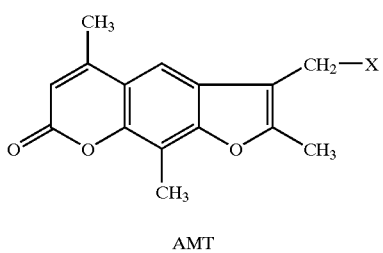

AMT

Another sensitizer which has also been used is 8-MOP which has the following structure:

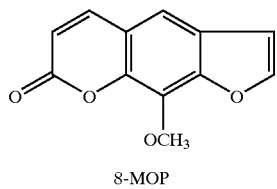

8-MOP

AMT was first prepared in 1977 and is commercially available. S-59 is the property of Cerus Corporation. 8-MOP and AMT are able to completely inactivate the virus, bacteriophage Φ6, in platelet concentrates under normal oxygen tension. Photoexcited psoralens react with cellular nucleic acids and lipids to some extent, but they react mainly with the amino acid residues of proteins in cells.

Unfortunately AMT and S-59 both have limited potency towards the non-enveloped parvoviruses. In addition, both of these sensitizers are themselves mutagenic, thus the treated blood product must be filtered after photolysis. Both of these sensitizers break down upon photolysis to a complex mixture of products of unknown toxicity thus the treated blood product must be filtered after photolysis. Moreover, AMT, 8-MOP, and S-59 accumulate in lipid membranes, and upon photolysis form triplet states, which sensitize the formation of singlet oxygen. The singlet oxygen so generated damages the lipid envelopes of platelets, thus antioxidants must be present to protect the platelets, and the oxygen concentration must be controlled. Accordingly, it is desirable to have new sensitizers that overcome some or all of these disadvantages of the currently available sensitizers.

The second aspect of the present invention relates to the use of flavin N-oxides, such as riboflavin N-oxide sensitizers to reduce pathogenic bacterial or viral contamination in compositions of blood products. Though not used to eradicate pathogenic contamination in blood products before, the flavin N-oxides are well suited for this purpose. Riboflavin N-oxide is electrically neutral and water soluble; it is also preferentially absorbed by bacteria and rapidly proliferating cells, and once it releases the radical that cleaves the nucleic acid, it forms vitamin B2, which is generally regarded as safe.

In the methods of the present invention, the flavin N-oxides are introduced to the composition containing the blood products. It is preferred that the flavin N-oxides of the present invention are water-soluble. By "water soluble" we mean that it is preferred that the solubility of the flavin N-oxides is at least 100 micromolar in water. An exemplary flavin N-oxide for the methods of the present invention is riboflavin N-oxide. Once introduced to the blood product composition, riboflavin N-oxide, which is electrically neutral, may passively transport into cells, where it is enzymatically activated to form a radical anion. Additionally, riboflavin N-oxide may be activated by electromagnetic radiation. When electromagnetic radiation is used as the activator, the wavelength of light is preferably in the visible region. Electromagnetic radiation in the range from about 400 to about 500 nm is desirable because it does not damage the blood products like ultraviolet radiation would.

When the activated radical anion in the cell encounters a spermidine-DNA complex, an acidic proton of the ammonium ion of the spermidine transfers to the radical anion. This converts the drug into a neutral radical, which fragments. In the case of riboflavin N-oxide the fragmentation will form riboflavin and hydroxyl radical. The hydroxyl radical will damage the nucleic acid. The riboflavin is simply vitamin B2, which is generally regarded as safe.

As red cells and plasma protein contain no nucleic acid-spermidine and platelets contain no genomic nucleic acid-spermidine, they cannot be damaged by this mechanism.

A typical efficacious dose of a flavin N-oxide is typically about 10 to about 100 μM, though the dose may need to be varied slightly depending on the flavin N-oxide that is used.

EXAMPLE 2

Inactivation of the Phage A flavin N-oxide, at a concentration of 10–100 μM, is added to solutions containing the non-enveloped right protein capsid phage T4. The oxygen concentration is carefully optimized as the flavin N-oxide may be more potent under hypoxic conditions. The solution is then exposed to visible light, preferably in the region from about 400 to about 500 nm, for a period of between 1 and 120 minutes. The extent of inactivation of the phage is then evaluated using a plaque assay. The extent of degradation of the compounds is evaluated by HPLC-MS analysis of reaction mixtures.

EXAMPLE 3

Inactivation of Parvovirus The flavin N-oxide, at a concentration of 10–100 μM, is added to solutions containing the non-envelope parvovirus. The oxygen content of the solutions is carefully optimized, and the solution is then exposed to visible light, preferably in the region from about 400 to about 500 nm, for a period of between 1 and 120 minutes. The extent of inactivation of the virus is then evaluated using a plaque assay. The extent of degradation of the compounds is evaluated by HPLC-MS analysis of reaction mixtures.

All documents referenced herein are incorporated by reference.

Although this invention has been described with respect to specific embodiments, the details of these embodiments are not to be construed as limitations.

The invention claimed is:

1. A method of treating a subject having a solid tumor, a non-solid tumor mass, leukemia, or non-small cell lung cancer comprising:
   a. administering a therapeutically effective amount of a flavin N-oxide to the subject; and
   b. exposing the flavin N-oxide to an activator, such that activation of the flavin N-oxide results in damage to the DNA in the cancer cells without substantial damage to the DNA in normal cells.

2. The method of claim 1 wherein the flavin N-oxide is of formula I:

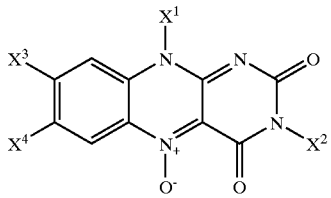

wherein $X^1$ is selected from H, monosaccharides, substitited monosaccharides, mono, di, and tri-ethylene glycol, alcohol, and alkyl ammonium ion; and $X^2$, $X^3$, and $X^4$ can be the same or different and are selected from H, monosaccharides, substitited monosaccharides, glycol, alcohol, lower alkyl, and alkylene groups;

wherein $X^2$, $X^3$, and $X^4$ can be substituted with monosaccharides, substitited monosaccharides, mono, di, and tri- ethylene glycol, alcohol, alkyl ammoniuni ion, and combinations thereof.

3. The method of claim 2 wherein the flavin N-oxide is riboflavin N-oxide.

4. The method of claim 1 wherein the activator comprises a reducing enzyme.

5. The method of claim 4 wherein the reducing enzyme is present in the cancer cells.

6. The method of claim 1 wherein the activator is electromagnetic radiation of sufficient wavelength and intensity to activate the flavin N-oxide.

7. The method of claim 6 wherein the electromagnetic radiation is X-ray radiation.

8. The method of claim 1 wherein the flavin N-oxide preferentially kills cancer cells rather than normal cells in a ratio of at least 5:1.

9. The method of claim 1 wherein the flavin N-oxide preferentially kills cancer cells rather than normal cells in a ratio of at least 10:1.

10. The method of claim 1 wherein the flavin N-oxide is used as part of a combination therapy.

11. The method of claim 10 wherein the combination therapy comprises radiation therapy.

12. The method of claim 10 wherein the combination therapy comprises chemotherapy.

13. The method of claim 10 wherein the combination therapy comprises chemotherapy and radiation therapy.

* * * * *